United States Patent
Trieu et al.

(10) Patent No.: US 6,605,090 B1
(45) Date of Patent: Aug. 12, 2003

(54) NON-METALLIC IMPLANT DEVICES AND INTRA-OPERATIVE METHODS FOR ASSEMBLY AND FIXATION

(75) Inventors: Hai H. Trieu, Cordova, TN (US); Jeff R. Justis, Cordova, TN (US); Troy D. Drewry, Memphis, TN (US); Michael C. Sherman, Memphis, TN (US); Bradley J. Coates, Rossville, TN (US); Bradley T. Estes, Memphis, TN (US)

(73) Assignee: SDGI Holdings, Inc., Wilmington, DE (US)

( * ) Notice: Subject to any disclaimer, the term of this patent is extended or adjusted under 35 U.S.C. 154(b) by 178 days.

(21) Appl. No.: 09/696,128

(22) Filed: Oct. 25, 2000

(51) Int. Cl.$^7$ .............................................. A61B 17/56
(52) U.S. Cl. ........................................................ 606/69
(58) Field of Search ........................... 606/69, 70, 71, 606/76, 78; 623/11.11, 16.11, 23.58, 23.75

(56) References Cited

U.S. PATENT DOCUMENTS

| | | |
|---|---|---|
| 4,193,899 A | 3/1980 | Brenner et al. |
| 4,781,183 A | 11/1988 | Casey et al. |
| 4,836,196 A | 6/1989 | Park et al. |
| 5,007,939 A | 4/1991 | Delcommune et al. |
| 5,084,050 A | 1/1992 | Draenert |
| 5,163,960 A | 11/1992 | Bonutti |
| 5,222,987 A | 6/1993 | Jones |
| 5,275,601 A | 1/1994 | Gogolewski et al. |
| 5,522,895 A | 6/1996 | Mikos |
| 5,569,250 A | 10/1996 | Sarver et al. |
| 5,578,034 A | 11/1996 | Estes |
| 5,593,425 A | 1/1997 | Bonutti et al. |
| 5,603,713 A | 2/1997 | Aust et al. |
| 5,607,427 A | 3/1997 | Tschakaloff |
| 5,634,926 A | 6/1997 | Jobe |
| 5,735,875 A | 4/1998 | Bonutti et al. |
| 5,800,544 A | 9/1998 | Demopulos et al. |
| 5,868,745 A | 2/1999 | Alleyne |

(List continued on next page.)

FOREIGN PATENT DOCUMENTS

| | | |
|---|---|---|
| DE | 4409833 | 10/1995 |
| FR | 2778088 | 11/1999 |
| FR | 2794963 | 12/2000 |
| GB | 2305483 | 4/1997 |
| WO | WO 99/44529 | 9/1999 |

OTHER PUBLICATIONS

Macrapore product information, http://www.macropore.com (undated).

Stachelin, Andreas C., "ACL–Restoration using semitendinosus tendon, Biosorbable Interference Screw," http://staehelin.ch/biosche.html, 1996.

Courtney, Patrick J., Serenson, James, "Adhesive Bonding of Medical Plastics: An Overview," *Medical Plastics and Biomaterials,* Jan. 1996.

(List continued on next page.)

*Primary Examiner*—Eduardo C. Robert
(74) *Attorney, Agent, or Firm*—Woodard, Emhardt, Moriarity, McNett & Henry LLP

(57) ABSTRACT

This invention relates to orthopedic implants and to methods of treating bone defects. More specifically, but not exclusively, the present invention is directed to non-metallic implants and to methods for intra-operative assembly and fixation of orthopedic implants to facilitate medical treatment. The non-metallic implant assembly can be secured to underlying tissue by a fastener, such as a bone screw, that is capable of swelling on contact with fluid in the underlying tissue. Alternatively, the non-metallic implant assembly can be assembled intra-operatively using a fastener that is adhesively bonded to a bone plate or the bone plate can be deformed using heat, force or solvents to inhibit withdrawal of the fastener. In preferred embodiments, both the fastener and the bone plate are formed of biodegradable material.

10 Claims, 10 Drawing Sheets

U.S. PATENT DOCUMENTS

| | | | |
|---|---|---|---|
| 5,868,746 | A | 2/1999 | Sarver et al. |
| 5,928,267 | A | 7/1999 | Bonutti et al. |
| 5,944,721 | A | 8/1999 | Huebner |
| 5,971,987 | A | 10/1999 | Huxel et al. |
| 6,007,539 | A | 12/1999 | Kirsch et al. |
| 6,022,352 | A | 2/2000 | Vandewalle |
| 6,059,817 | A | 5/2000 | Bonutti et al. |
| 6,071,982 | A | 6/2000 | Wise et al. |
| 6,090,996 | A | 7/2000 | Li |
| 6,093,201 | A | 7/2000 | Cooper et al. |
| 6,206,883 | B1 | 3/2001 | Tunc |
| 6,221,075 | B1 | 4/2001 | Törmälä et al. |
| 6,322,562 | B1 * | 11/2001 | Wolter ................. 606/69 |
| 6,331,179 | B1 * | 12/2001 | Freid et al. ............. 606/61 |

OTHER PUBLICATIONS

Varanese, Donald V., "The Fundamentals of Selecting Pressure–Sensitive Adhesives," *Medical Plastics and Biomaterials,* Jan. 1998.

Middleton, John D.; Tipton, Arthur J., "Synthetic Biodegradable Polymers as Medical Devices," *Medical Plastics and Biomaterials Magazine,* Mar. 1998.

Sofamor Danek, "ATLANTIS Anterior Cervical Plate System," 1998.

Sofamor Danek Group, "Meeting the Needs of Spinal and Cranial Surgeons Worldwide," 1998.

Sofamor Danek, "ORION, Anterior Cervical Plate System," 1999.

Medtronic Sofamor Danek, "DYNALOK Plus Spinal System," 1999.

Zdeblick, Thomas A., "ZPLATE II Anterior Fixation System, Surgical Technique," Medtronic Sofamor Danek, 1999.

Sigot–Luizard, M.F., "Evaluation Biologique du Composite Osta–Pek (Carbone–Pekekk) Utiliséen Chirurgie Rachidienne," *Rachis Revue de Pathologie Vertebrale,* vol. 12, No. 1, May 2000.

* cited by examiner

NON-METALLIC IMPLANT DEVICES AND INTRA-OPERATIVE METHODS FOR ASSEMBLY AND FIXATION

BACKGROUND OF THE INVENTION

The present invention relates to orthopedic implants and to methods of treating bone defects. More specifically, but not exclusively, the present invention is directed to non-metallic orthopedic implants, methods for intra-operative assembly of the orthopedic implants, and methods of internal fixation of bone tissue to facilitate medical treatment.

It is known to use orthopedic implants, such as plates, rods, and screws, to repair and treat bone defects, such as cracked and broken bones, and disorders of the musculo-skeletal system. In the past, many of the orthopedic implants were formed primarily of metallic materials. The metallic implants offer many advantages. They can be readily sterilized, are biocompatible, and provide the requisite strength for support and/or fixation of the bony tissue. However, metallic implants also exhibit a significantly greater compressive modulus over cortical bone. The metallic implant can stress-shield new bone growth to induce osteoporosis and/or osteopenia, resulting in cortical bone that is prone to refracture. After the bone defect was repaired, often the implants were no longer needed to maintain the patient's mobility. While some metal implants were allowed to remain in place, many were removed. Their removal required a second surgical procedure. Obviously, it would be more desirable to eliminate the second surgical procedure to minimize patient pain/discomfort, chance of infection, and subsequent trauma to the newly healed site, while at the same time removing the implant as a potential source of irritation for surrounding tissue.

More recently, new treatment methods and improved materials, including non-metallic implants, have been used to treat bone defects. The non-metallic implants can remain in the body, or alternatively, selected implants can be made of materials that biodegrade over a time period ranging from a few days to several months.

While the new materials have provided significant advances over the previous medical devices, there still remain significant problems requiring continued development for non-metallic medical implants—not the least of which is their lower of mechanical strength compared with their metallic counterparts. Typically, non-metallic orthopedic implants have not provided sufficient strength to be used alone for internal fixation of load-supporting bone tissue, such as the long bones of the upper and lower limbs and the spine. Further, selected non-metallic implants such as bone plates can fail when installed with non-metallic bone fasteners. Reduced friction between contacting surfaces of fastener and bone plate; lower mechanical strength; lower holding force; and in selected materials, biodegradation of the implants themselves, to name a few examples, all can contribute to an unacceptable failure rate for the non-metallic implants. Even metallic fasteners have been known to dislodge or back out from the implant and/or bone tissue. The non-metallic fasteners can be even more prone to dislodge. The non-metallic fasteners cannot be tightened or torqued sufficiently to prevent the fastener from disengaging from the plate. The non-metallic bone screws do not exhibit the mechanical strength of metal counterparts, and typical mechanical lock mechanisms and techniques often fail to maintain an integral connection with non-metallic fasteners—requiring revision surgery. This can be acerbated for implants formed from biodegradable materials, which successively degrade over time and which become increasingly weaker as they degrade. These are but a few of the problems faced by patients and their physicians in selecting an appropriate course of treatment.

In light of the above-described problems, there is a continuing need for advancements in the relevant field, including improved methods, compositions and devices to provide non-metallic implants that exhibit a high rate of successful orthopedic and musculoskeletal treatment and yet reduce necessity for subsequent surgical intervention. The present invention is such an advancement and provides a wide variety of benefits and advantages.

SUMMARY OF THE INVENTION

The present invention relates to orthopedic implants and to the manufacture and use thereof. Various aspects of the invention are novel, nonobvious and provide various advantages. While the actual nature of the invention covered herein can only be determined with reference to the claims appended hereto, certain forms and features which are characteristic of the preferred embodiments disclosed herein are described briefly as follows.

In one form, the present invention provides an implant assembly that comprises a bone plate having at least one opening extending therethrough and a bone fastener received within the opening. The bone fastener has a proximal head, a bone engaging distal portion and a shaft therebetween. The fastener, the bone plate, or both, are formed of a polymeric material capable of deforming to fixedly interengage the fastener to the bone plate.

In another form, this invention provides an implant assembly that comprises a bone plate having an opening extending therethrough, and a fastener that is received within the opening. The fastener has a head, a threaded distal portion and a shaft therebetween. At least a portion of the fastener is formed of a polymeric material capable of swelling upon contact with body fluid to fixedly secure the fastener to the bone plate.

In another form, this invention provides an implant assembly comprising a bone plate having at least one opening extending therethrough, and a fastener that is to be received within the opening. The fastener has a proximal head, a distal bone engaging portion and a shaft therebetween. At least one of the fasteners and the bone plate include an adhesive to fixedly interengage the fastener to the bone plate.

In yet another form, this invention provides a method of fixedly securing a fastener to a bone plate. The method comprises surgically preparing bone tissue in need of repair for receipt of a bone plate; placing a bone plate having at least one opening proximal to the bone tissue in need of repair; and inserting a fastener through the opening and into the bone tissue. At least one of the fastener and the bone plate is deformed to fixedly secure the bone screw to the bone plate.

In still yet another form, this invention provides a method of fixedly securing a bone screw to a bone plate. This method comprises surgically preparing bone tissue in need of repair for receipt of a bone plate; placing a bone plate having at least one opening therethrough proximal to the bone tissue; and inserting a bone screw through the opening and into the bone tissue. At least one of the fastener and the bone plate include an adhesive to fixedly secure the fastener to the bone plate.

Further objects, features, aspects, forms, advantages and benefits shall become apparent from the description and drawings contained herein.

DETAILED DESCRIPTION OF THE INVENTION

For the purposes of promoting an understanding of the principles of the invention, reference will now be made to the embodiments illustrated herein and specific language will be used to describe the same. It will nevertheless be understood that no limitation of the scope of the invention is thereby intended. Any alterations and further modifications in the described processes, systems or devices, and any further applications of the principles of the invention as described herein, are contemplated as would normally occur to one skilled in the art to which the invention relates.

In general, one form of the present invention includes an implant comprising a bone plate or other suitable remedial orthopedic structure and a bone fastener. The bone fastener can be used to secure the bone plate to the bone tissue to maintain the desired position of the implant. In a more specific form, the implant is securely positioned during surgery by fixedly interengaging the bone fastener to the bone plate and the bone tissue. The bone fastener can be secured to the bone plate with a variety of techniques and in various configurations. In one form, the bone fastener is mechanically secured to the bone plate, preferably, by deformation of either the fastener, the bone plate or both. In alternative forms, the bone fastener can be adhesively secured to the bone plate. In still yet another form, the bone fastener can be formed of material that swells upon contact with body fluids, such that the bone fastener is mechanically secured to the bone tissue to inhibit fastener pullout.

Figure 1:
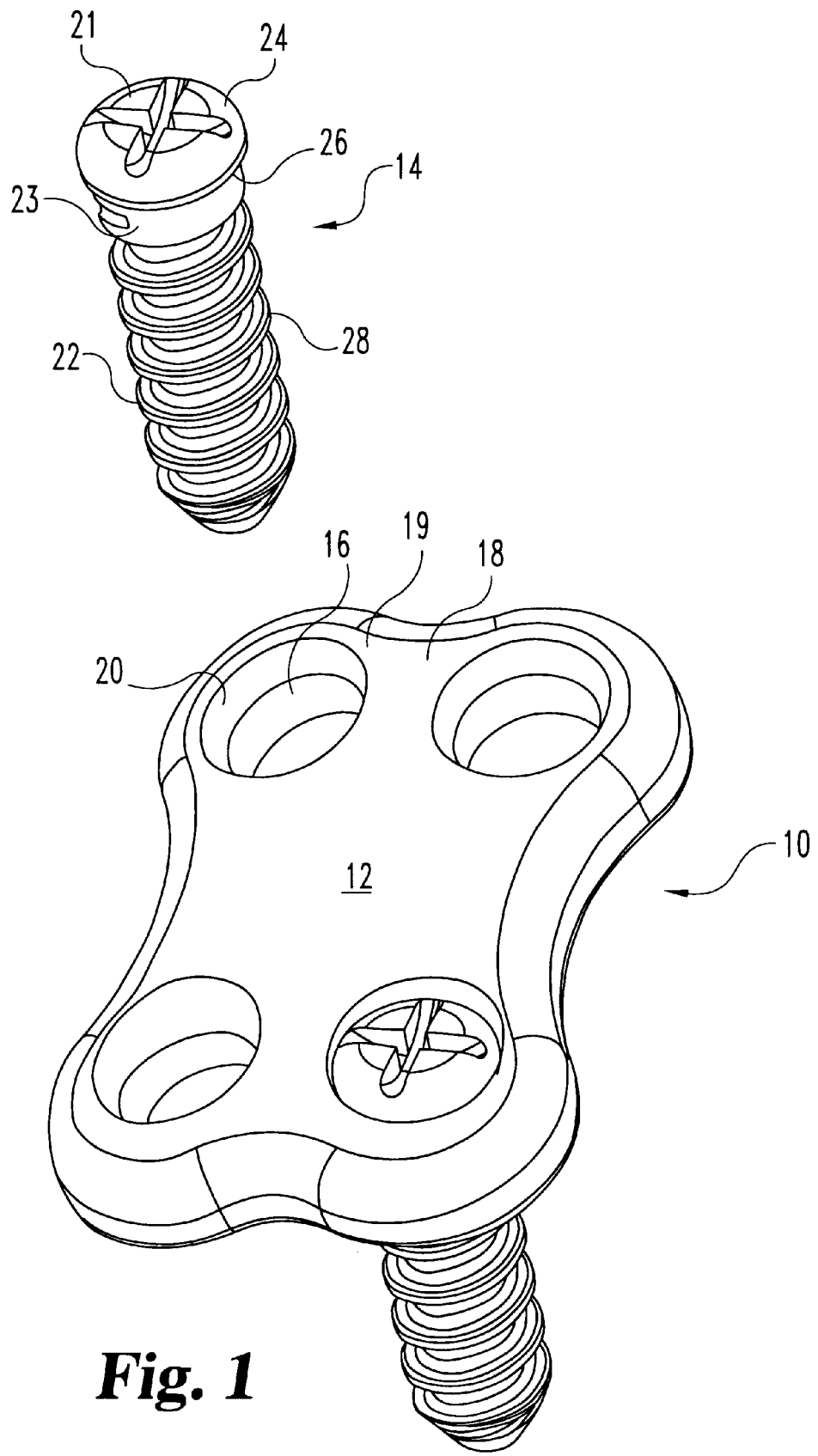
FIG. 1 is a perspective view of one embodiment of a non-metallic bone plate and of a non-metallic fastener according to this invention.

FIG. 1 illustrates one embodiment of an implant 10 that includes a bone plate 12 and a bone fastener 14, respectively. Bone plate 12 includes at least one opening 16 for receipt of a portion of the bone fastener therethrough. It is understood that plate 12 is a stylized configuration of a bone plate or suitable remedial orthopedic implant and that bone plate 12 can be formed in various configurations. (See, for example, FIGS. 9A–16.) Preferred configurations conform anatomically to bone tissue or other tissue to be treated. Alternatively, bone plate 12 can be configured to a desired configuration to provide a support structure for rehabilitation of damaged or diseased bone tissue. It will be further understood that plate 12 is sufficiently rigid to provide bone fixation for treatment of bone defects, such as cracks, breaks, and other bone deformities, and correct alignment of adjacent bone structures, for example, adjacent vertebral bodies.

Bone plate 12 can be formed of a non-metallic material, such as polymeric, composite materials, with or without reinforcement such as fibers, fillers, platelets, and the like. Examples of suitable materials are discussed below. Alternatively, bone plate 12 can be formed of a metallic material and fixedly secured to bone tissue using a non-metallic fastener such as fastener 14.

Opening 16 is adapted to receive a portion of fastener 14. Preferably, opening 16 provides a recess or countersunk section 20 so that the head 21 of fastener 14 can be recessed below the upper surface 18 of bone plate 12. Additionally, opening 16 can be deformed with mechanical energy, heat energy, solvent or a combination thereof to fixedly engage fastener 14. In the illustrated embodiment, opening 16 is depicted as a substantially circular opening. In alternative forms, opening 16 can be provided in a variety of configurations, for example, as an oblong opening or a slot, to allow intra-operative positioning of bone plate 12 and/or fastener 14. This invention provides particular advantages for securing a fastener in a particular location within a slot formed in a bone plate. The fastener is securedly in the slot to one location. Once the fastener is secured to the underlying tissue, even in the absence of additional securing means, the plate does not shift or move with respect to the underlying tissue.

Material 19 adjacent to opening 16 can be deformed to partially block or overlay opening 16. In one form, deformation of material 19 forms a dimple in the upper surface 18 of plate 12. (See, for example, an alternative embodiment of implant assembly in FIGS. 4 and 5.) In yet another alternative, deformation of material 19 provides a substantially smooth upper surface 18.

Fastener 14 is provided with a head 21, a tissue-engaging portion 22, and a connecting shaft 23 therebetween. Head 21 is imprinted for receipt of a Phillips-type driving tool. The specific imprint or tool-engaging structure is not critical for this invention; and accordingly, it is within the scope of the present invention to include fasteners having various drive-tool-engaging structures associated with head 21. In addition head 21 can be configured with a curved or rounded upper profile 24. Underside lip 26 of head 21 is configured to matingly engage in recessed section 20 of plate 12. In one form, fastener 14 is fixedly interengaged with plate 12 by deformation of material 19 about opening 16. In alternative forms, fastener 14 is deformed to interengage material within opening 16 and/or underlying tissue to prevent backout from plate 12 and increase its holding tenacity to underlying tissue. (See, for example, FIGS. 5A/B and 7.)

Tissue-connecting portion 22 is connected to head 21 with connecting shaft 23. Preferably, but not required, connecting shaft 23 is formed without external threads. Further, connecting shaft 23 can be provided in a variety of lengths and outside diameters (OD). In one form, connecting shaft 23 provides merely a juncture between head 21 and tissue-engaging portion 22. Further, connecting shaft 23 can be formed of a material to allow the joining of two dissimilar materials—one material for head 21 and a second material for tissue-engaging portion 22.

Tissue engaging portion 22 includes external threads 28. In a preferred embodiment, fastener 14 is provided as the self-tapping screw. Therefore external threads 28 are sufficiently rigid to bore into bone tissue. When so provided, underlying tissue need not be pre-drilled to provide an opening for receipt of tissue engaging portion 22. Alternatively, fastener 14 can be provided in a variety of configurations with and without threads. For example, fastener 14 can be provided as a pin (not shown). The pin can, but is not required, to include additional structures extending laterally from the bone-engaging portion to engage with and potentially extend into adjacent bone tissue.

Figure 2:
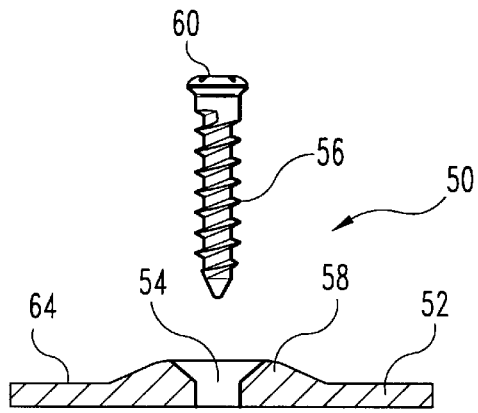
FIG. 2 is side elevation view of an alternative embodiment of a deformable bone plate and fastener according to the present invention.

FIG. 2 illustrates one embodiment of a deformable implant assembly 50 according to the present invention. Implant assembly 50 includes a deformable bone plate 52 having at least one opening 54 formed therein and a bone fastener 56 is provided to be received within the opening 54 to secure plate 52 to tissue such as bone (not shown).

Bone plate 54 is provided to secure fastener 56. In the illustrated embodiment, bone plate 52 includes a deformable portion 58 adjacent to opening 54. Deformable portion 58 substantially encircles opening 54 providing a collar or cone-like structure extending beyond surface 64. In alternative forms, the deformable portion need not completely encircle opening 54. Further, deformable portion 58 can be provided in a variety of configurations other than cone-like structure, including ridges, tabs, rings and the like. The alternative structures need not extend beyond surface 64 of plate 52. Deformable portion 58 and bone plate 52 can be formed of the same material or of different materials, which are bonded or formed together. Examples of specific materials are discussed below.

Figure 3:
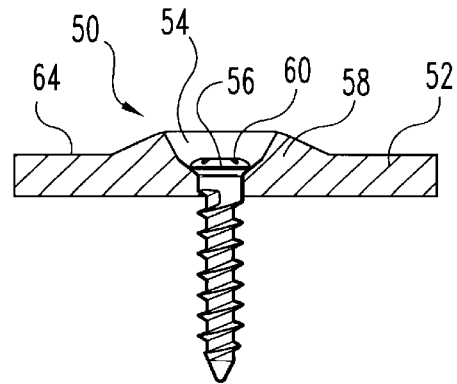
FIG. 3 is a side elevation view illustrating the interengagement of the fastener and deformable bone plate of FIG. 2.
Figure 4:
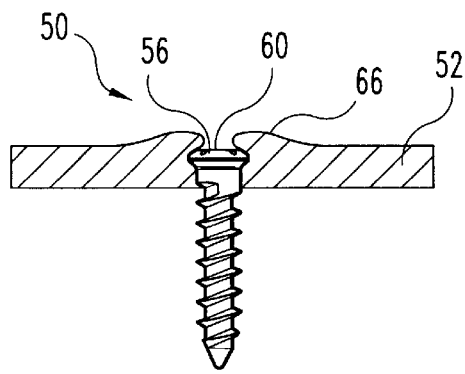
FIG. 4 is a side elevation view illustrating the deformation of the bone plate and fastener of FIG. 3.

Referring additionally to FIGS. 3 and 4, which illustrate receipt and subsequent fixation of fastener 56 into opening 54, fastener 56 is inserted into opening 54, preferably such that head 60 of fastener 56 is received below the upper surface 64 of plate 52. After fastener 56 has been received within opening 54, the deformable portion 58 can be deformed to provide a mechanical lock to prevent retropulsion of fastener 56 from opening 54. It is preferable, but not necessary, that the deformable portion bear against head 60. It is sufficient that a portion of the deformable portion 58 overlay a portion of opening 54 and head 60 to inhibit withdrawal of fastener 56 from opening 54.

Deformable portion 58 can be deformed either upon application of heat, force and/or solvent. Any suitable heat generating apparatus can be used to heat and deform the material in portion 58. Examples of heating apparatus include a hot air gun, a small welding or soldering gun, ultra sonic welders or a Bovie tip. Also usable are lasers, which are commonly provided in operating rooms. Lasers are especially desirable because they are precise and controlled in their application, can generate sufficient heat very quickly, and cause less thermal necrosis because there is less misdirected heat. The heating process can be done pre-operatively to form an implant assembly. Alternatively, the heating process can be done outside the body, but in the operating room, to customize implants at the time of surgery; or can be done during surgery, in the body, when assembly of the implant is desired within the body.

Similarly, any suitable force that can be applied either pre-operatively or intra-operatively can be used. One preferred example includes the use of ultra sonic devices, which can deform plastic material with little or minimal heat generation.

Alternatively, solvents can be used to deform a portion of the bone screw. Typically solvents that soften the plastic material are selected. Such solvents can include organic-based solvents and aqueous-based solvents, including body fluids. Care should be taken that the selected solvent is not contra indicated for the patient, particularly when the solvent is used intra-operatively. The choice of solvents will also be selected based upon the material to be deformed. Examples of solvents that can be used to deform a portion of the bone plate include alcohols, glycols, glycol ethers, oils, fatty acids, acetates, acetylenes, ketones, aromatic hydrocarbon solvents and chlorinated solvents.

In addition to deforming portion 58, any of the above-discussed techniques and apparatus can also be used to bond fastener 56 to plate 52.

Referring specifically to FIG. 4, deformed portion 66 overlays a portion of head 60 to prevent fastener 56 from backing out of plate 52. In the illustrated embodiment, deformed portion 66 resembles a circular mound with a centered dimple or recess revealing the top of head 60. It will be understood that, in practice, the configuration of deformation may vary depending on the method and instrumentations used to deform the material. For example, it is not necessary that the top of head 60 be visible, nor is it necessary that deformed portion 66 completely encircle opening 54 and/or fastener 56.

Figure 5:
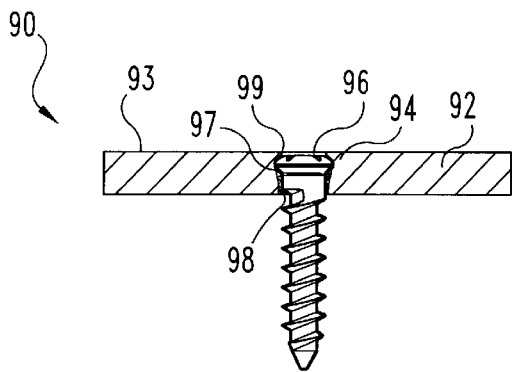
FIG. 5 is a side elevation view of an alternative embodiment of the interengagement of a bone plate and fastener.

FIG. 5 depicts an alternative embodiment of an implant assembly 90 comprising a bone plate 92 having a substantially planar upper surface 93 and at least one opening 96 formed therethrough. Bone plate 92 includes a malleable or deformable portion 94 adjacent to opening 96. Deformable portion 94 can be deformed by application of heat and/or mechanical energy, or solvents, as previously described for implant assembly 50. In one form, bone plate 92 is initially provided in a configuration substantially as described for bone plate 52 of FIG. 2. The substantially flush upper surface 93 can be formed by heating the deformable material 94, causing it to flow into the bore 97 of opening 96—with or without the addition of force—to urge the material into bore 97. Preferably, deformable material 94 can be worked into bore 97 by the application of force. The resulting deformable material 99 overlays a portion of fastener 98 received within opening 96. The amount of deformable material 94 provided on plate 92 can vary and depend upon a number of factors including the selection of deformable material, the composition of the fastener and the plate, the diameter of the opening 96, the diameter of fastener 98, and the amount, if any, the deformed material extends beyond upper surface 93.

If desired, any portion of deformable material 94 protruding above the upper surface 93 can be removed by cutting or planing. When thus provided, the resulting implant assembly 90 provides a smooth outer surface to reduce irritation to adjoining tissue overlaying upper surface 93.

Figure 6A:
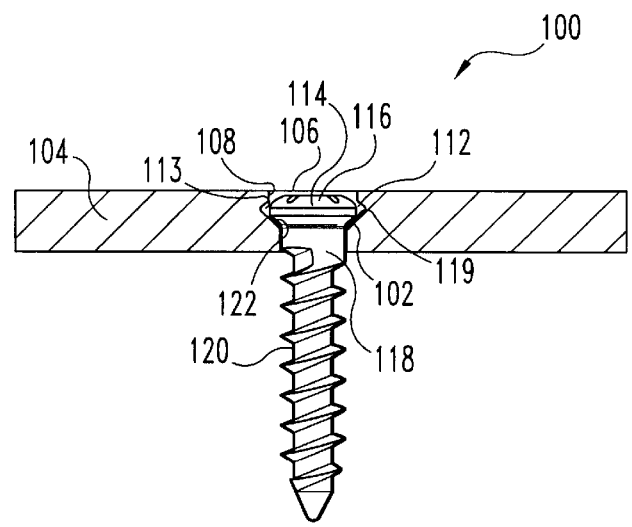
FIG. 6A is a side elevation view of one embodiment of a bone plate and deformable fastener for use with this invention.
Figure 6B:
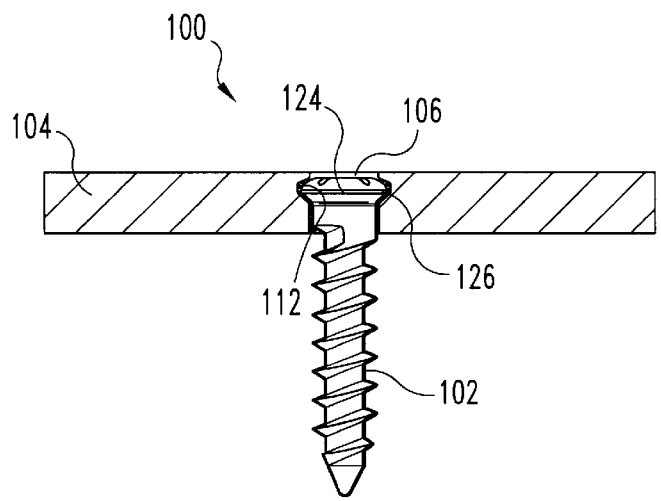
FIG. 6B is a side elevation view illustrating the deformation of the fastener and bone plate of FIG. 6A.

FIGS. 6A and 6B illustrate yet another embodiment of a deformable fastener and bone plate assembly 100. Assembly 100 includes at least one deformable fastener 102 and a bone plate 104 having at least one opening 106 formed therethrough. Opening 106 defines an internal bore 108 having a circumferential recess 112 axially positioned therein. Recess 112 is illustrated as having a concave surface 113 extending about the entire circumference of bore 108. It is intended that recesses having a wide variety of internal surface configurations come within the scope of this invention. The various recess configurations need not completely encircle bore 108. In alternative embodiments, recess 112 can also include a wide variety of structural features to inhibit rotation of a deformed fastener received within bore 108. Examples of these structural features include roughened or knurled surfaces, as well as grooves and/or ridges extending axially through bore 108. Bore 108 also includes a fastener bearing surface 119 positioned axially from recess 112.

Referring specifically to FIG. 6A, deformable fastener 102 is depicted prior to deformation. Fastener 102 includes a head 114 having a deformable portion 116, connecting shaft 118, and tissue engaging portion 120. Deformable portion 116 of head 114 includes additional material capable of being deformed upon application of heat energy or work energy. Head 114 is configured with a drive tool engaging structure as described for head 21 of fastener 14. Underneath surface 122 of head 108 overhangs connecting shaft 118. When fastener 102 is fully received within opening 106, underneath surface 122 bears against fastener bearing surface 119 and prevents head 108 from being driven completely through opening 106.

Referring now specifically to FIG. 6B, deformed fastener 124 is depicted in opening 106 in a deformed state. Deformed portion 126 expands to substantially fill recess 112. The deformed portion effectively inhibits removal or backing out of fastener 102 from opening 106. Deformed portion 126 can be deformed using techniques and instruments as previously described for implant assembly 50. Deformed portion can be prepared from any suitable material; specific examples are discussed below.

Figure 7:
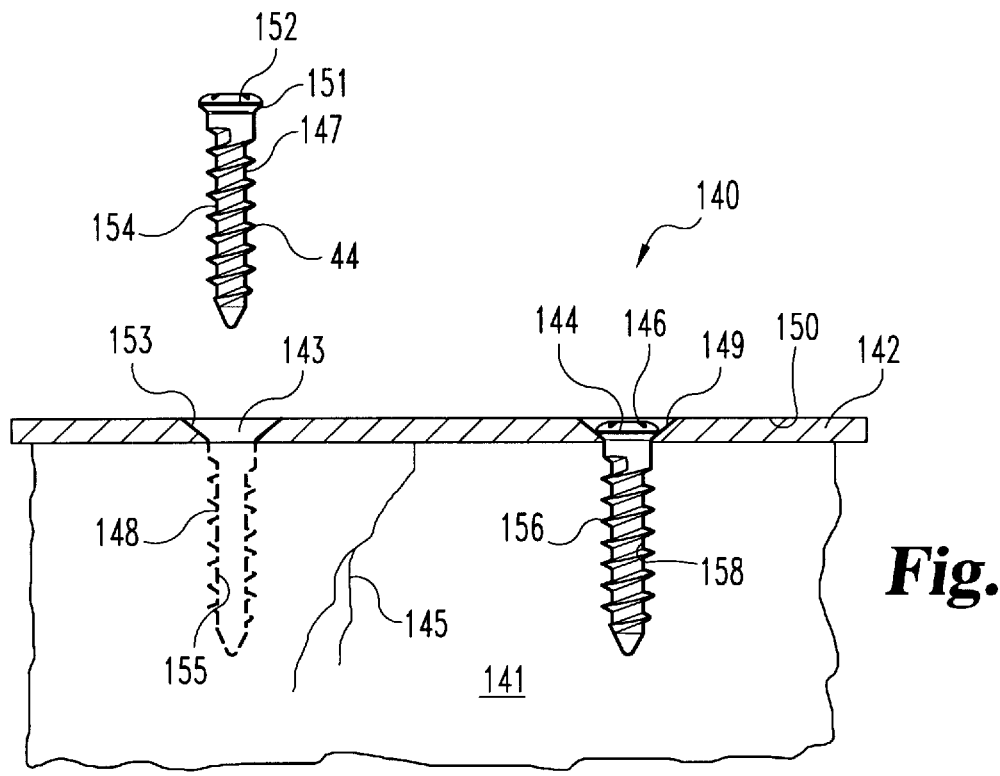
FIG. 7 is side elevation view of one embodiment of a deformable bone plate and fastener secured to bone tissue.

FIG. 7 depicts an implant assembly 140 comprising plate 142 and at least one fastener 144. Implant assembly 140 is illustrated as partially secured to bone tissue 141 bridging defect 145, which is presented as a crack or break in bone tissue 141. Bone plate 142 includes at least one opening 143 positioned on one side of defect 145 and at least one second opening 144 positioned on the opposite side of defect 145. If desired or required for optimum treatment, plate 142 can have multiple openings for receipt of an equal number of fasteners. Bone fastener 146 is depicted within opening 144 and engaged to tissue 141 such that head 149 of fastener 146 is positioned below the upper surface 150 of plate 142. Second bone fastener 147 is illustrated adjacent to opening 143 in plate 142 and pre-drilled hole 148 in tissue 141. It is understood that openings 143 and 144 may be pre-formed in bone plate 142. Alternatively, openings 143 and 144 may be located and bored during surgery. Fabrication of bone plate 142 out of nonmetallic materials facilitates locating and drilling openings 143 and 144 intra-operatively. Typically, non-metallic materials are much softer and therefore easier to drill than their metallic counterparts. First bone fastener 146 is received within opening 144 and threadedly secured to bone tissue 141.

In operation, fastener 147 is inserted through opening 143 theadedly engaged into predrilled hole 148 in tissue 141. Predrilled hole 148 can be tapped or untapped to threadedly receive fastener 147. Fastener 147 is advanced so that an underneath portion 151 of head 152 bears against beveled surface 153 of opening 143. This fixedly secures bone plate 142 to bone tissue 141.

In the illustrated embodiment, tissue-engaging portion 154 of second fastener 147 is formed of a material that is capable of swelling upon contact with body fluid. Immediately upon contacting bone tissue 141 or subsequent thereto, tissue-engaging portion 154 begins absorbing body fluid typically contained within the tissue. This causes the tissue-engaging portion 154 to swell and mechanically interlock with internal tissue 141 and/or the walls 155 of opening 148 to fixedly secure both screw 147 and bone plate 142 to tissue 141. Tissue-engaging portion 154 can be formed of a material selected to absorb body fluid, for example, blood, serum, plasma, and the like, found in body tissues. A variety of materials can be selected to provide the bone-engaging portion capable of swelling in contact with body fluid. Non-limiting examples include oligomers, homopolymers, co-polymers, and polymer blends that include polymerized monomers derived from d, l and d/l lactic acid (lactide) and glycolic acid (glycolide) caprolactone, amides, and mixtures of these monomers. Examples of polymers, co-polymers and polymer blends for use in the this invention include, but are not limited to: l, d, d/l, polyactide, polyglycolide, poly (lactide-co-glycolide), tyrosine-derived polycarbonate, polyanhydride, polyorthoester, and polyphosphazene. Further, the capability of a polymeric material to swell can be modified by varying the degree of polymerization, crystalinity and composition of the polymer. Use of the term co-polymers is intended to include within the scope of the invention polymers formed of two or more unique monomeric repeating units. Such co-polymers can include random copolymers, graft copolymers, block copolymers, radial block, diblock, triblock copolymers, alternating co-polymers, and periodic co-polymers.

It can be observed in FIG. 7 that the tissue-engaging portion 156 of fastener 146 is swollen. In preferred embodiments, the swollen tissue-engaging portion bears against the bone tissue surface internal to the predrilled hole 158. Further, it should be understood that the tissue-engaging portion 156 swells sufficiently to effectively inhibit removal of second fastener 146 from opening 144 primarily through a mechanical interlock mechanism.

Figure 8:
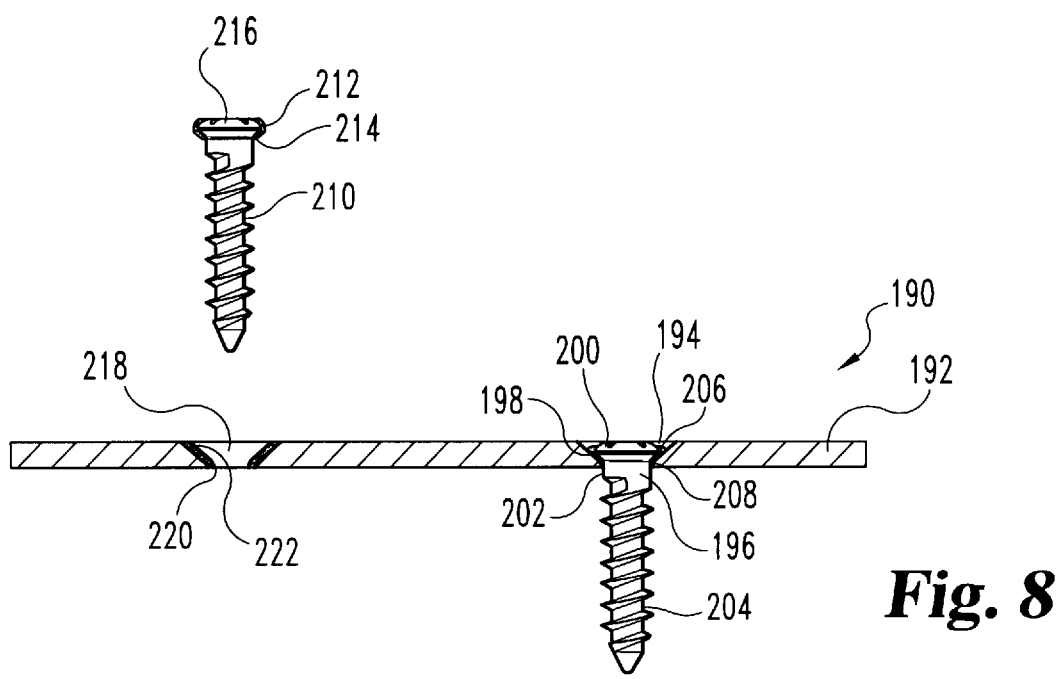
FIG. 8 is a side elevation view of a non-metallic fastener adhesively bonded to a bone plate according to this invention.

FIG. 8 provides yet another embodiment of an implant assembly 190 according to the present invention. Implant assembly 190 includes a bone plate 192 having at least one opening 194 formed therethrough, and a bone fastener 196 received within the at least one opening 194. As discussed earlier, bone fastener 196 includes a head 200, a tissue-engaging portion 204, and a connecting shaft 202 therebetween. Fastener 196 is fixedly secured to bone plate 192, preferably by bond 206.

Fastener 196 can be secured to the bone plate by solvent bonding. In this form, it is preferable that the fastener and bone plate be formed of compatible material amenable to solvent welding. Typically a solvent—often an organic solvent—is applied to both surfaces, i.e., the underside surface 208 of head 200 and inner surface 198. The solvent softens and can dissolve a portion of the material. Once the material is sufficiently plastic, the fastener is advanced through opening 194 and into underlying tissue until surface 208 contacts surface 198. The solvent is then removed by evaporation with or without the addition of heat. The resulting implant assembly is sufficiently bonded together, preferably by semi-interpenetrating polymer network, for a time sufficient to promote healing of the bone defect. As with the previously described implant assemblies, the bone fastener 196 and bone plate 192 can be made of biodegradable material.

Fastener 196 can also be adhesively bonded at the interface between the inner surface 198 of the at least one opening 194 and an underneath surface 208 of head 200. The adhesive to bond fastener 196 to bone plate 192 is selected to be biocompatible, preferably biodegradable. Examples of adhesives for use in the present invention include cyanoacrylate, epoxy, polyester, polyolefin, polyurethane, silicone adhesives, and known derivatives thereof. The adhesive can be cured by applying heat, free radical initiated either chemically by light and/or radiation.

The adhesive can also be selected to be either a one-part or a multi-part adhesive. The one-part adhesive may be applied either to the bone fastener 210 and/or bone plate 192. When the adhesive is selected to be a multi-part adhesive, at least one part of the adhesive 212 can be provided on the bone fastener 210, preferably on the underside surface 214 of head 216, and a second part of the adhesive 220 can be provided on the bone plate 192 in the inner surface 222 of opening 218.

In the embodiment depicted in FIG. 8, fastener 214 is illustrated as bone screw. This configuration provides distinct advantages for a multi-part adhesive system. When fastener 214 is threadedly engaged with underlying bone tissue, the first part of the adhesive 212 on underneath surface 214 initially contacts the second part of the adhesive 220 on the inner surface 222. Continued rotation of fastener 214 serves to intermix the two parts of the adhesive to provide a homogenous multi-part adhesive. This homogenous multi-part adhesive can rapidly cure to form a strong adhesive bond between bone fastener 110 and bone plate 192.

The present invention can also include a pressure-sensitive adhesive. The pressure-sensitive adhesive can be provided in either a single-part or a multi-part adhesive as described above. Pressure-sensitive adhesives provide advantages over other adhesives, which often require cure time. For example, pressure-sensitive adhesives have distinct abilities to bond dissimilar materials together. They also can form strong, adherent bonds to human tissue, and there is no need for a lengthy cure time or initiator, such as light or heat, to initiate curing of the adhesive. The pressure-sensitive adhesive can be applied to the tissue-engaging portion of the fastener. Once the fastener is implanted into the tissue, it can secure the attached bone plate. The pressure-sensitive adhesive can be selected to provide sufficient adhesion and sufficient shear strength to maintain the bone fastener within the at least one opening 194. Further, the pressure-sensitive adhesive can be preapplied to either bone plate 192 and/or fastener 196. This can be applied during the manufacturing process of either component. Alternatively, the adhesive can be applied during or immediately before surgical procedures. When the pressure-sensitive adhesive is applied in manufacturing processes, it is desirable to include a non-adherent covering such as a removable backing paper to cover the portion of the implant covered by the adhesive. This allows the adhesive to be handled and shipped without adversely affecting the adhesive and maintains clean, substantially non-contaminated surfaces, although it should be understood that the components should be sterilized prior to any surgical procedures. When desired, the pressure-sensitive backing can be removed from covering the adhesive so that the two components can be secured together.

The pressure-sensitive adhesive can be selected from a wide variety of known compounds. Examples include: acrylics adhesives, silicon adhesives, polyester adhesives and polyurethane adhesives. As with the above-mentioned adhesive, the pressure-sensitive adhesives can be provided in one or multi-part components.

Typically the release backing includes a silicon-coated paper that can be readily removed immediately before or during surgical procedures. After removal of the backing, the bone fastener is threadedly engaged or advanced through an opening in a bone plate. As mentioned before, the bone fastener can be either a pin or a threaded bone fastener such as a bone screw. When a bone screw is used, the bone screw can be advanced into a predrilled hole in the bone tissue. Alternatively, the bone screw can be self-tapping. Once a portion of the fastener, preferably the underside surface of a fastener head, bears against the bone plate, for example, inner surface of an opening formed in the bone plate; the adhesive can be allowed, to cure. Typically curing times are relatively short, lasting between seconds to several minutes. Once the adhesive has cured, the bone fastener is fixedly secured to bone plate such that it does not back out or loosen during normal, recommended physical activities of the patient.

Figure 9A:
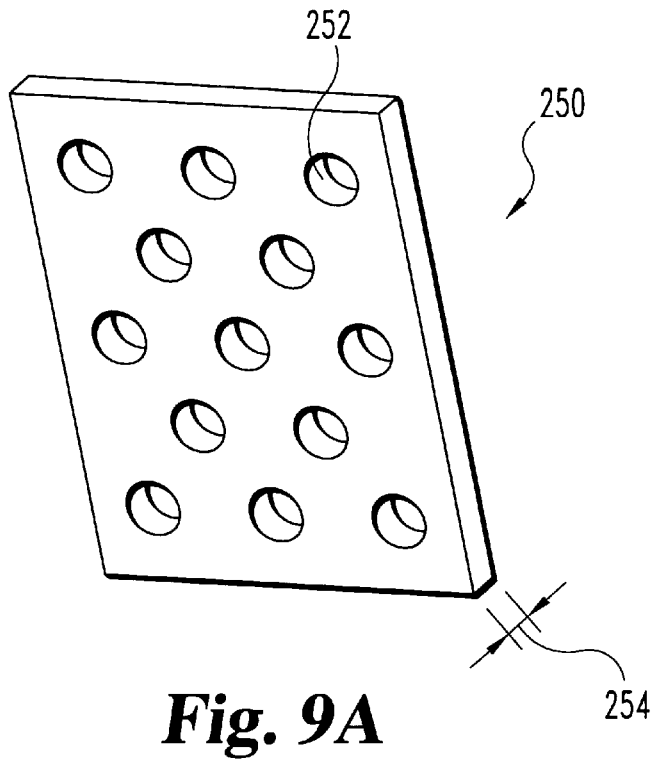
FIG. 9A is a perspective view of one embodiment of a single-level deformable vertebral plate for this invention.
Figure 9B:
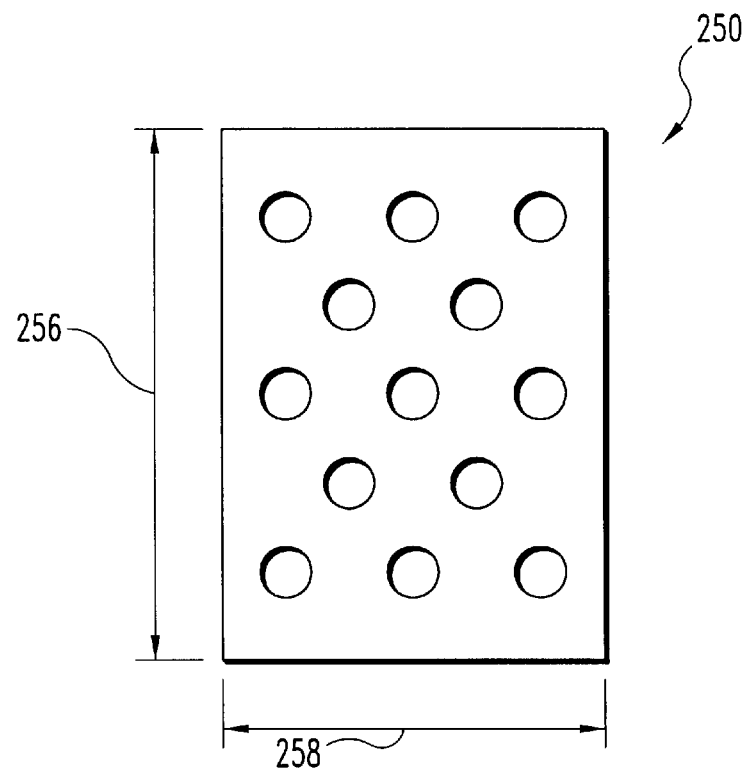
FIG. 9B is a top plan view of the vertebral plate of FIG. 9A.

FIGS. 9A and 9B illustrate one example of a flexible plate 250 for use with thesis invention. Plate 250 includes multiple openings 252 for variations for attachment to anatomical structures. The multiple openings provide the surgeon with multiple options for fixation and correction of bone and muscular tissue. The surgeon can select the number of fasteners and the specific opening through which to insert the fasteners, depending upon the available healthy tissue, its condition, and the overall anatomy or macrostructure of bone tissue.

In one form, bone plate 250 can be used to facilitate reattachment or strengthening of ligaments and/or tendons to bone structures. The location and size of the multiple openings 252 can be provided to enhance the flexibility of bone plate 250 to allow sufficient mobility and articulation of joined bodies and tissues. In addition bone plate 250 has a thickness represented by reference line 254 selected to further facilitate flexibility yet maintain sufficient strength to maintain fixation of the joined bodies. In preferred embodiments, the thickness of bone plate 250 is selected to be between about 0.5 mm and about 4 mm; more preferably, between about 1.5 mm and about 2.5 mm. It is also understood that the flexibility of bone plate 250 can be varied by varying either its thickness, the number and location of the multiple openings 252, or the material used to form it.

In one preferred embodiment, the bone plate is provided as a single-level plate suitable for attachment to adjacent vertebral bodies, for example, to attach adjacent lumber vertebra and either re-attach, strengthen or replace a damaged anterior longitudinal ligament (ALL). The implanted bone plate can improve extension of the patient's spine after surgery—yet still maintain desired disc height between the co-joined vertebrae. In this embodiment, plate 250 has a height, represented by reference line 256, that is selected to be between about 20 mm and about 60 mm; more preferably between about 40 mm and about 50 mm. Similarly, the width of bone plate 250, represented by reference line 258, is selected to be equal to about ⅛ to about ⅓ of the circumference of a particular vertebral body. The width can be selected to be between about 10 mm and about 40 mm; more preferably between about 15 mm and about 20 mm.

Figure 10A:
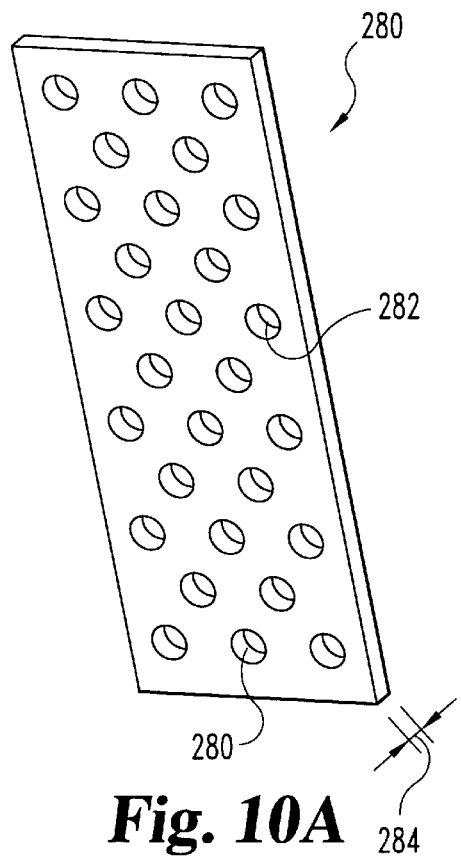
FIG. 10A is a perspective view of one embodiment of a two level deformable vertebral plate for this invention.
Figure 10B:
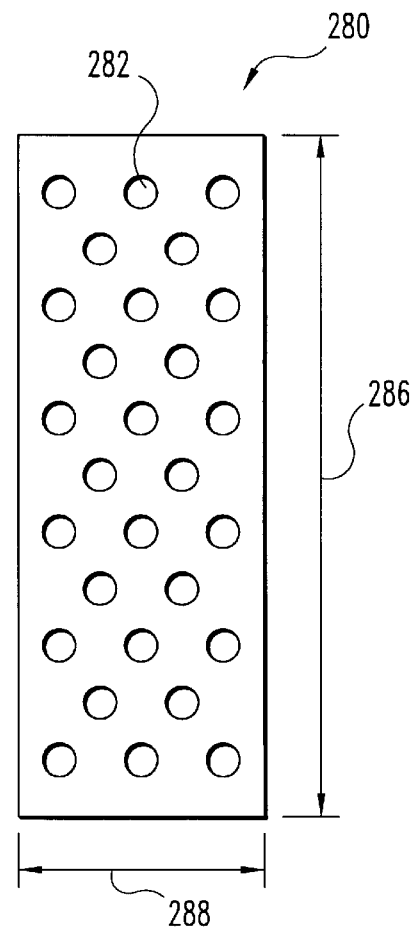
FIG. 10B is a top plan view of the vertebral plate of FIG. 10A.

FIGS. 10A and 10B are illustrations of a two-level bone plate 280 for use with this invention. Bone plate 280 can be provided substantially as described for bone plate 250. Plate 280 includes a plurality of openings 282 formed therethrough to receive fasteners as has been described above. Bone plate 280 has a thickness represented by reference line 284 suitable to provide sufficient flexibility to repair and/or replace ligaments that connect bone structures. In one preferred embodiment, bone plate 280 is sized to have a thickness between about 0.5 mm and about 4.5 mm; more preferably between about 1.5 mm and about 2.5 mm.

Figure 11:
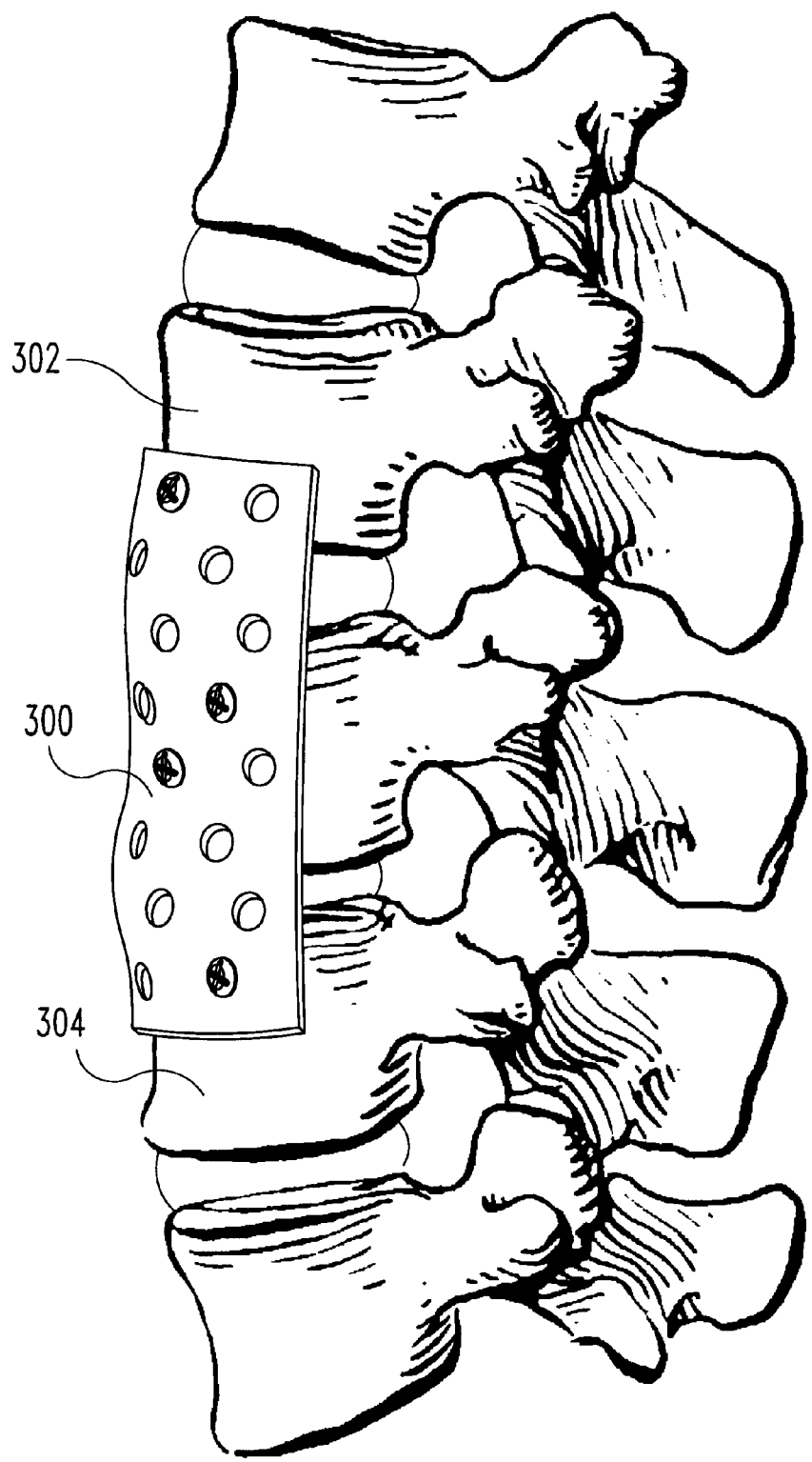
FIG. 11 is a side elevation view of the deformable plate of FIG. 10A, securing three lumbar vertebrae.

Bone plate 280 is sized for attachment to three adjacent vertebral bodies (See, for example, FIG. 11.) Preferably bone plate 280 has a height represented by reference line 286, selected to be between about 50 mm and about 120 mm; more preferably between about 80 mm and about 100 mm. Bone plate 280 has a width represented by reference line 288, selected to be about ⅛ to about ⅓ of the circumference of a particular vertebral body. The width can be selected to be between about 10 mm and about 40 mm; more preferably between about 15 mm and about 20 mm.

Both bone plates 250 and 280 have a plurality of openings, 252 and 282, respectively. The openings can be provided to include deformable portions as described for plates 12, 52, and 92. Further, bone plates 250 and 280 can be attached to tissue using a variety of fasteners described above including fasteners 14, 98, 102, and 143.

In preferred embodiments, bone plates 250 and 280 are formed of a moldable or malleable material. Thus the plates can be molded either prior to or during a surgical procedure to conform to an anatomical structure such as the anterior facet of a vertebra. Examples of suitable material include both resorbable and non-resorbable listed below.

FIG. 11 illustrates placement and deformation of a bone plate substantially as described for FIGS. 10A and 10B above. Bone plate 300 extends from a first lumbar vertebra 302 to a third lumber vertebra 304. Bone plate 300 can be deformed to conform to a desired anatomical structure either prior to the operation or during the operation.

Figure 12:
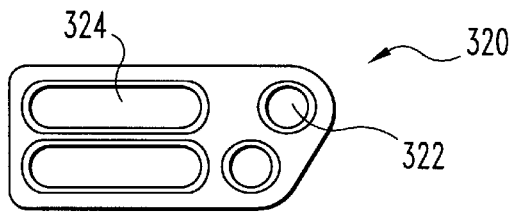
FIG. 12 is a top plan view of one embodiment of a deformable plate suitable for use in anterior fixation of the spine according to this invention.

FIG. 12 illustrates a deformable bone plate 320 for use in the present invention. Plate 320 can include a wide variety of openings extending therethrough. In the illustrated embodiment, plate 320 includes at least one circular opening 322 and one slot 324 extending therethrough. Plate 320 can be provided in a variety of sizes adapted to extend from one vertebral body to an adjacent vertebral body. Alternatively, plate 320 can be provided in sizes to extend over a plurality of vertebral bodies.

Figure 13:
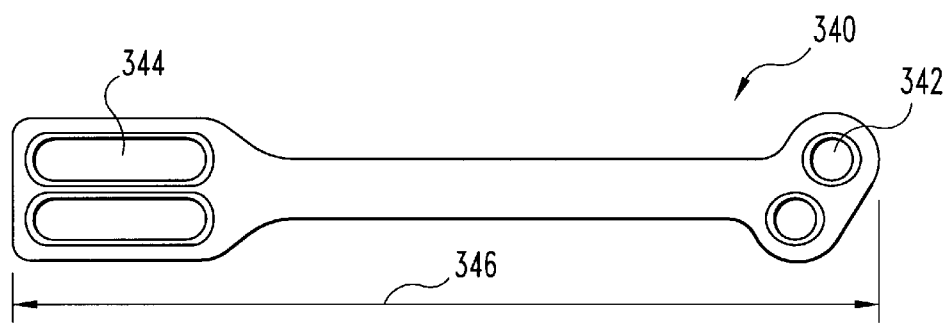
FIG. 13 is a top plan view of another embodiment of a deformable plate suitable for use in anterior fixation of the spine according to this invention.

FIG. 13 illustrates an alternative embodiment of a bone plate 340. Bone plate 340, similar to bone plate 320, can include a wide variety of openings extending therethrough. Bone plate 340 includes at least one circular opening 342 and at least one slotted opening 344 extending therethrough. Bone plate 340 is provided to have a length represented by reference line 346 that can be variable. In preferred embodiments, length of bone plate 340 can be between about 5 cm and about 15 cm; more preferably, bone plate 340 is provided in a length between about 7 cm and about 13 cm.

Figures 14A, 14B:
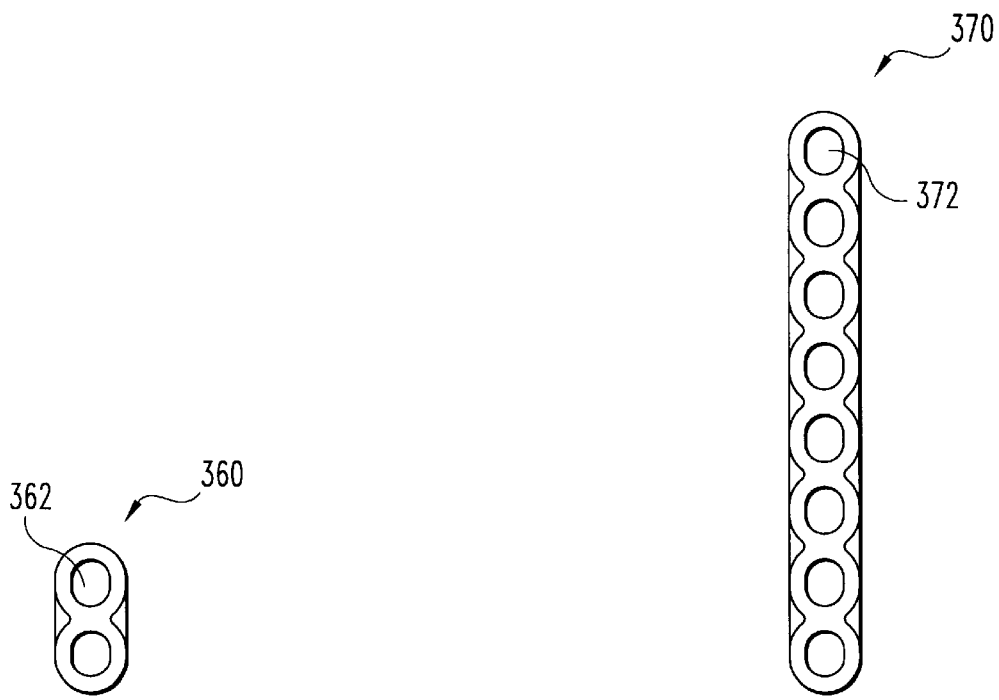
FIG. 14A is a top plan view of one embodiment of a single level deformable plate for use in this invention.
FIG. 14B is a top plan view of one embodiment of a multilevel deformable plate for use with this invention.

FIGS. 14A and 14B illustrate yet another embodiment of a deformable bone plate for use in the present invention. FIG. 14A illustrates a bone plate 360 provided with at least two openings 362 extending therethrough. FIG. 14B illustrates deformable bone plate 370 having a plurality of openings 372 extending therethrough. Both bone plates 360 and 370 are illustrated as an elongate plate having at least two, more preferably, a plurality of openings extending therethrough. The openings are positioned along the length of bone plate 360 and 372; preferably positioned uniformly along the length of the elongate plates 360 and 370. It is also included within the scope of the invention that either bone plate 360 or bone plate 370 can be provided with a fewer number of openings or a single elongate opening, for example a slot. During surgery, a surgeon can locate and then subsequently drill through either one or the other bone plate 360 or 370 to provide an additional opening to fasten the respective bone plates to bone tissue.

Figure 15:
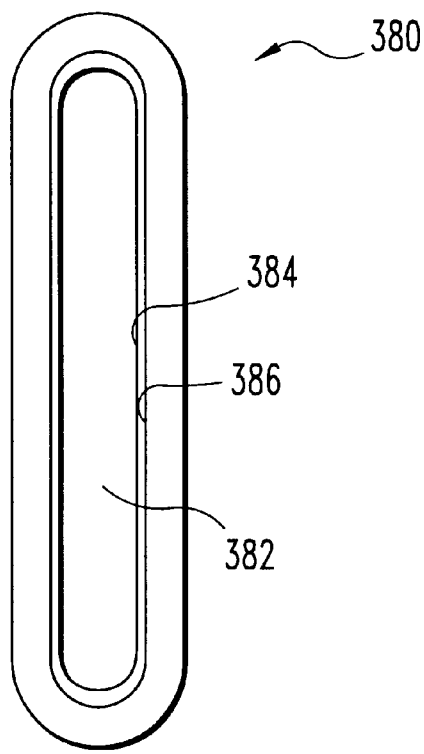
FIG. 15 is a top plan view of one embodiment of a deformable plate for use in posterior fixation of the spine according to this invention.

FIG. 15 illustrates still yet another embodiment of a deformable bone plate 380 for use in the present invention. The deformable bone plate is an elongate plate having at least one slot 382 extending therethrough. In alternative embodiments, slot 382 can include a series of of elliptical surfaces extending the length of slot 382. Elliptical surfaces can matingly engage in the underneath surface of a fastener, for example, fastener 14 of FIG. 1. As with the other bone plates discussed above, bone plate 380 can be provided in a wide variety of sizes. The size of bone plate 380 can be selected depending upon the particular bone structure to which plate 380 is to be attached.

Figure 16:
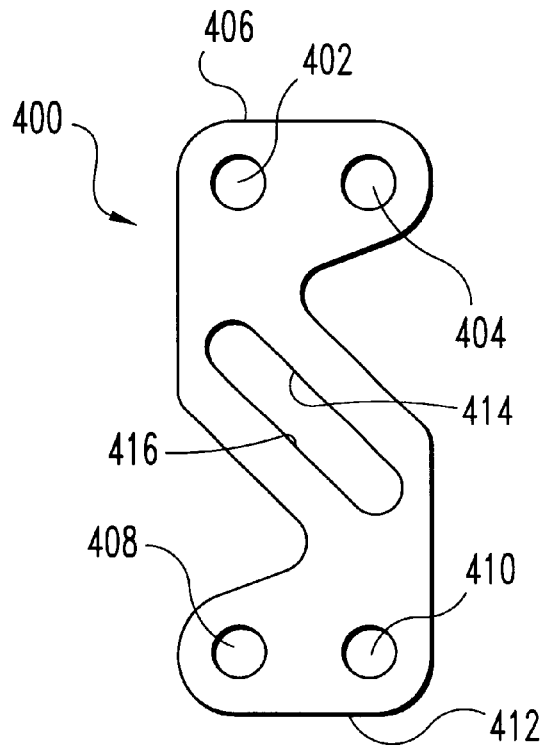
FIG. 16 is a top plan view of one embodiment of a deformable plate suitable for fixation of cervical vertebrae according to this invention.

FIG. 16 illustrates still yet another embodiment of a deformable bone plate 400 for use in the present invention. Bone plate 400 can be adapted to provide a fixation of cervical vertebrae. Bone plate 400 can include a wide variety of openings and slots formed therethrough. In the illustrated embodiment, bone plate 400 includes at least a pair of openings 402 and 404 positioned on a first end 406 of plate 400. Additionally, openings 408 and 410 are provided on the opposite end 412. Additionally, plate 400 can include at least one slot 414 formed therethrough. Slot 414 can be provided with a substantially smooth interior surface 416. Alternatively, slot 414 can be provided with elliptical interior surfaces as has been described for plate 380 in FIG. 15.

Figure 17:
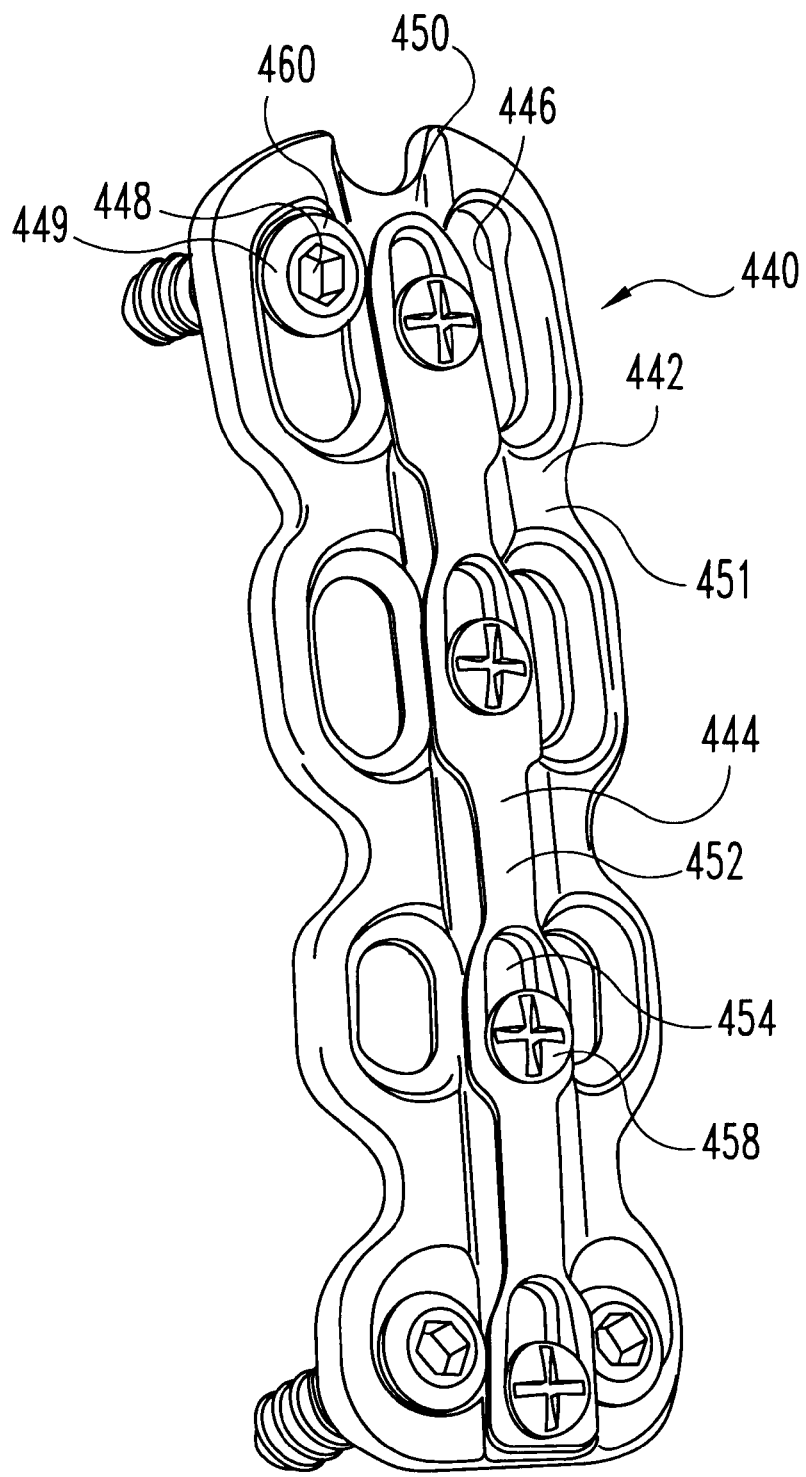
FIG. 17 is perspective view on one embodiment of a bone plate assembly for use in this invention.

FIG. 17 depicts still yet another embodiment of a deformable bone plate assembly 440. Plate assembly 440 includes a bone plate 442 and at least one anti-migration portion 444 moveably mounted to plate 442. Plate 442 includes a plurality of openings 446 through which one or more bone fasteners 448 are inserted. It is preferable—but not required—that fasteners 448 are bone screws 449. Openings 446 can be provided substantially as described above—particularly for plates 15, 52 and 92. Groove 450 in nonbearing surface 451 extends along the length of plate 442. At least one tapped opening is formed in groove 450. Plate 442 can be formed of a polymeric material that is either biodegradable or a non-biodegradable polymer. Additionally plate 442 can be formed of a metal such as titanium or surgical steel. Preferably, plate 442 is formed of a deformable polymer and is readily shaped or contoured during surgery to conform to the anatomical configuration of the targeted bone structure. In a preferred form, plate 442 is configured to connect two adjacent cervical vertebrae and can be used to promote spine fusion.

In the illustrated embodiment, anti-migration portion 444 includes a bar 452 slidably received within groove 448 and having at least one, more preferably, a series of oblong openings 454 extend through bar 452. Oblong openins 454 permit slidable attachment of bar 452 to plate 442 with a threaded fastener 458. Anti-migration portion 444 can include a variety of other structural features in addition to or in substitution to bar 452. For example anti-migration portion 444 can include a movable structure to overlay a portion of the head 460 of fasteners 448. To that end anti-migration portion 444 can include screws, pivotally mounted wings, slidably mounted caps and the like. In these embodiments, anti-migration portion moves from a first position that allows withdrawal or insertion of a fastener 448 to a second position that inhibits withdrawal or insertion of fastener 448.

Ant-migration portion 444 is made of a material that is the same as the material for plate 442. Alternatively, anti-migration portion 444 is made of a dissimilar material. For example, anti-migration portion 444 can be made of metal and bone plate 442 can be made of a polymeric material or anti-migration portion can be made of a polymeric material and bone plate 442 made of metal.

Bone plates having the generalized configurations described above or alternative plates that exhibit a similar mode of operate include implants sold under the trade names ATLANTIS, AXIS, DYNALOK, DYANALOK PLUS, PREMIER, Z-PLATE II, and ZEPHIR by Medronic Sofamor Danek of Memphis Tennessee.

Preferably prior to use, the plates, fasteners and adhesives described in this invention are sterilized, most likely chemically, using ethylene oxide gas or irradiating the components with gamma radiation. Typically, sterilization procedures using low temperatures are required of non-metallic components, such as the bone fastener and/or the bone plate. The chemical and radiation-type sterilizations usually are selected to not affect the properties or performance of the adhesives. When the adhesive is provided on one or more of the components during manufacturing, preferably the portion of the implant covered by the adhesive is covered with a release backing that can withstand the sterilization procedures.

It is understood for the embodiments of the invention as disclosed herein, either the bone fastener or the bone plate, or both, can be made of a non-metallic material. Alternatively, it is understood that the bone plate can be made of a metallic material while the bone fastener is made of a non-metallic material. Typical examples of resorbable materials for constructing the devices of the invention include: Polyhydroxyacids, e.g. poly(L-lactide, poly(D-lactide), poly(L/D-lactide), poly (L/DL-lactide), polyglycolide, copolymers of lactide and glycolide of various compositions, copolymers of said lactides and/or glycolide with other polyesters, copolymers of glycolide and trimethylene carbonate, polyhydroxybutyrate, polyhydroxyvalerate, copolymers of hydroxybutyrate and hydroxyvalerate of various compositions, polyorthoesters, polyanhydrides, polydioxanone, polydioxanediones, polyesteramides, polymalic acid, polyesters of diols, oxalic and/or succinic acids, polyamino acids, copolymers of amino acids and glutamic acid, polyamides, polycaprolactone, polycarbonates. Preferred degradable polymers (homopolymers/copolymers) are polylactides, polyglycolide, polydioxanone, poly/glycolide-co-trimethylene carbonate), poly(lactide-co-glycolide), and polyesteramides.

Examples of non-degradable polymeric materials useful in the present invention include, but are not restricted to: acrylic, fluorocarbon, hydrogel, polyacetal, polyamide, polycarbonate, polyester, polyaryletherketone polyimide, polyolefin, polystyrene, polysulfone, polyurethane, poly (vinyl chloride), silicone rubbers, polyethylene, and polyetherketones, e.g., PEK, PAEK, PEEK, PEKEKK, and mixtures thereof.

The polymeric material can be a thermoplastic or a thermoset. The polymeric materials can be formed as a composite or matrix and include reinforcing material or phases such as fibers, rods, platelets and fillers. For example, the polymeric material can include glass fibers, carbon fibers, polymeric fibers, ceramic fibers, and the like. In preferred embodiments the polymeric material is formed without any inclusion of reinforcing material such as carbon fibers, glass fibers, ceramic particulates or fillers.

While the invention has been illustrated and described in detail in the drawings and foregoing description, the same is considered to be illustrative and not restrictive in character, it is understood that only the preferred embodiments have been shown and described and that all changes and modifications that come within the spirit of the invention are desired to be protected.

What is claimed is:

1. An implant assembly comprising:

a bone plate having an upper surface and an opposite tissue engaging surface and at least one opening extending therethrough, and a bone fastener comprising a proximal head, a bone engaging distal portion and a shaft therebetween, wherein the bone plate is deformed to overlay an upper most surface of said head of the fastener to inhibit withdrawal of the fastener from the at least one opening.

2. The implant assembly of claim 1 wherein said bone plate includes a thermally deformable collar substantially encircling said opening.

3. The implant assembly of claim 2 wherein the collar deforms to overlay a portion of the proximal head.

4. The implant assembly of claim 1 wherein at least one of the bone plate and the fastener are formed of a biodegradable material.

5. The implant assembly of claim 1 wherein the fastener is formed of a polymeric material comprising homopolymers, co-polymers and oligomers of polyhydroxy acids, polyesters, polyorthoesters, polyanhydrides, polydioxanone, polydioxanediones, polyesteramides, polyaminoacids, polyamides, polycarbonates, polylactide, polyglycolide, tyrosine-derived polycarbonate, polyanhydride, polyorthoester, polyphosphazene, polyethylene, polyester, polyvinyl alcohol, polyacrylonitrile, polyamide, polytetrafluorethylene, poly-paraphenylene terephthalamide, polyaryletherketones, polyetherketones, cellulose, carbon fiber reinforced composite, and mixtures thereof.

6. The implant assembly of claim 1 wherein at least one of the fastener and the bone plate are formed of a polymer comprising monomeric repeating units derived from d-lactic acid, l-lactic acid, glycolic acid, caprolactone, hydroxy buteric acid, hydroxy valeric acid, and mixtures thereof.

7. A method of fixedly securing a fastener to a bone plate, said method comprising:

surgically preparing bone tissue in need of repair for receipt of a bone plate;

placing a bone plate having at least one opening proximal to said bone tissue in need of repair; and inserting a fastener through the at least one opening and into the bone tissue; and deforming a portion of the bone plate to overlay an upper most surface of a head of the fastener.

8. The method of claim 7 wherein said inserting comprises deforming a portion of the bone plate with application of thermal energy to overlay a portion of the fastener.

9. The method of claim 7 wherein said inserting comprises deforming a portion of the bone plate or the fastener upon application of ultrasonic energy.

10. An orthopedic device comprising:

a bone plate having at least one opening therethrough and formed of a polymeric material;

a fastener comprising a first end defining a head having a surface configured to engage a drive tool and an opposite, second end defining a tissue engaging portion, said fastener disposed within the at least one opening wherein a portion of the bone plate overlays a portion of said surface and the tissue engaging portion projects therefrom.

* * * * *